(12) United States Patent
Hyde et al.

(10) Patent No.: US 8,280,520 B2
(45) Date of Patent: Oct. 2, 2012

(54) SYSTEMS CONFIGURED TO LOCATE A PHOTONIC DEVICE DISPOSED IN A LIVING SUBJECT, AND RELATED APPARATUSES AND METHODS

(75) Inventors: Roderick A. Hyde, Redmond, WA (US); Muriel Y. Ishikawa, Livermore, CA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 822 days.

(21) Appl. No.: 12/316,811

(22) Filed: Dec. 15, 2008

(65) Prior Publication Data
US 2010/0070002 A1 Mar. 18, 2010

Related U.S. Application Data

(63) Continuation-in-part of application No. 12/283,911, filed on Sep. 15, 2008.

(51) Int. Cl.
*A61N 1/00* (2006.01)
(52) U.S. Cl. .......................................... 607/60
(58) Field of Classification Search .................... 607/33, 607/60, 61
See application file for complete search history.

(56) References Cited

U.S. PATENT DOCUMENTS

| 5,320,098 | A | 6/1994 | Davidson |
| 5,387,259 | A * | 2/1995 | Davidson ..................... 600/310 |
| 6,898,464 | B2 | 5/2005 | Edell et al. |
| 2007/0027505 | A1 * | 2/2007 | Ginggen ........................ 607/60 |

OTHER PUBLICATIONS

Roderick A. Hyde et al., U.S. Appl. No. 12/283,911, filed Sep. 15, 2008, "Systems Configured to Transmit Optical Power Signals Transdermally Out of a Living Subject, and Devices and Methods".
Roderick A. Hyde et al., U.S. Appl. No. 12/378,152, filed Feb. 11, 2009, "Systems Configured to Power At Least One Device Disposed in a Living Subject, and Related Apparatuses and Methods".

* cited by examiner

*Primary Examiner* — Eric D. Bertram
(74) *Attorney, Agent, or Firm* — Workman Nydegger

(57) ABSTRACT

In an embodiment, a system includes a biocompatible photonic device configured for disposal within a living subject and a location-indicating aid associated with the photonic device. The location-indicating aid is configured to facilitate locating the biocompatible photonic device within the living subject. Related apparatuses and methods of use are also disclosed.

24 Claims, 5 Drawing Sheets

SYSTEMS CONFIGURED TO LOCATE A PHOTONIC DEVICE DISPOSED IN A LIVING SUBJECT, AND RELATED APPARATUSES AND METHODS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/283,911, entitled SYSTEMS CONFIGURED TO TRANSMIT OPTICAL POWER SIGNALS TRANSDERMALLY OUT OF A LIVING SUBJECT, AND DEVICES AND METHODS, naming RODERICK A. HYDE, MURIEL Y. ISHIKAWA, DENNIS J. RIVET, ELIZABETH A. SWEENEY, LOWELL L. WOOD, JR., AND VICTORIA Y. H. WOOD as inventors, filed 15 Sep. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In an embodiment, a system includes a biocompatible photonic device configured to be disposed within a living subject and a location-indicating aid associated with the photonic device. The location-indicating aid is configured to facilitate locating the biocompatible photonic device within the living subject.

In an embodiment, an apparatus configured for disposal within a living subject includes a photonic device configured to (1) receive one or more optical power signals transmitted transdermally into the living subject and convert the one or more optical power signals into electrical energy; or (2) convert electrical energy into one or more optical power signals transdermally transmittable out of the living subject. The apparatus also includes a location-indicating aid configured to facilitate locating the photonic device within the living subject. The apparatus further includes a biocompatible packaging enclosing at least the photonic device.

In an embodiment, a method includes transmitting one or more first signals to a living subject. The method further includes, responsive to the transmitting, receiving one or more second signals transmitted from the living subject indicative of a location of a photonic device disposed within the living subject.

In an embodiment, a method includes receiving one or more first signals transmitted from a living subject. The method also includes targeting an optical-electrical converter disposed within the living subject based at least partially on information associated with the one or more first signals. The method further includes transmitting one or more optical power signals transdermally into the living subject and to the targeted optical-electrical converter.

In an embodiment, a method includes transmitting one or more signals from a living subject that are indicative of a location of an optical-electrical converter disposed within the living subject. The method also includes receiving one or more optical power signals with the optical-electrical converter, which are transmitted transdermally into the living subject responsive to the transmitting. The method further includes converting the one or more optical power signals into electrical energy using the optical-electrical converter.

In an embodiment, a method includes receiving a query at a transceiver associated with a photonic device, wherein the transceiver and the photonic device are disposed within a living subject. The method further includes, responsive to the receiving the query, transmitting location information about the photonic device transdermally out of the living subject from the transceiver.

In an embodiment, a method includes providing location information about a location of a photonic device disposed within a living subject.

In an embodiment, a method includes receiving one or more first signals transmitted from a living subject. The method also includes locating an electrical-optical converter disposed within the living subject based at least partially on information associated with the one or more first signals. The method further includes receiving one or more optical power signals transmitted transdermally out of the living subject and to an external device.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

DETAILED DESCRIPTION

Figure 1:
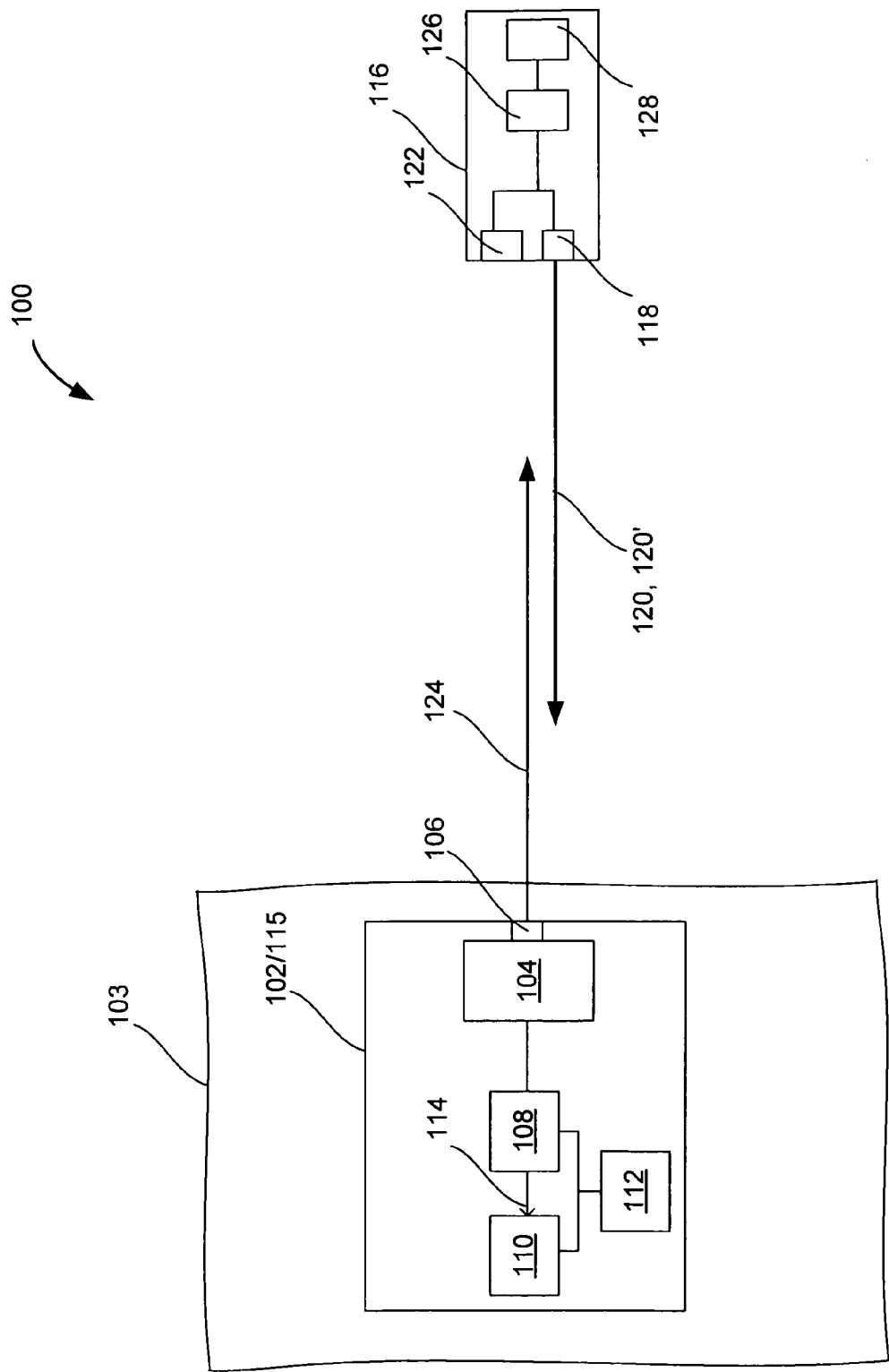
FIG. 1 is a functional block diagram of an embodiment of a system including a biocompatible photonic device disposed within a living subject and a location-indicating aid configured to facilitate locating the biocompatible photonic device.

Embodiments disclosed herein are directed to systems configured to locate a photonic device (e.g., an optical-electrical converter or an electrical-optical converter) disposed in a living subject, apparatuses configured to be disposed in a living subject including a photonic device and a location-indicating aid configured to facilitate locating the photonic device in a living subject, and methods of locating a photonic device disposed in the living subject. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

FIG. 1 is a functional block diagram of an embodiment of a system 100 including a biocompatible photonic device disposed within a living subject and a location-indicating aid configured to facilitate locating the biocompatible photonic device. Referring to FIG. 1, the system 100 includes a biocompatible apparatus 102 configured to be disposed within a living subject 103, such as being embedded in tissue, muscle, or bone of a human being. The apparatus 102 includes an optical-electrical converter 104 (e.g., one or more photodiodes), a retroreflector 106 positioned at least proximate to an optical receiving surface of the optical-electrical converter 104, and an energy-storage device 108 (e.g., a battery or a capacitive device) coupled to receive and store electricity received from the optical-electrical converter 104. For example, the retroreflector 106 may be configured as a corner cube, a reflective/refractive optical device, or another suitable reflective structure configured to reflect electromagnetic radiation away from the optical-electrical converter 104 and generally in the direction from which it was emitted. As will be discussed in more detail below, the retroreflector 106 functions as a location-indicating aid that facilitates locating the optical-electrical converter 104 disposed within the living subject 103 from outside of the living subject 103.

Still referring to FIG. 1, the apparatus 102 further includes at least one device 110, and control circuitry 112 coupled to the at least one device 110 and the energy-storage device 108. The at least one device 110 may be configured as a number of different biomedical devices. For example, the at least one device 110 may be configured as at least one of a drug delivery device, a micro-electro-mechanical device, a bone extension device, a biosensor, a neurostimulator, or other suitable biomedical device. The control circuitry 112 is configured to control distribution of electricity from the energy-storage device 108 to the at least one device 110 as one or more electrical power signals 114 that power the at least one device 110 and the operation of the at least one device 110. The control circuitry 112 may be powered by its own dedicated power source or may be configured to use a small amount of power from the energy-storage device 108 for power.

The optical-electrical converter 104, retroreflector 106, energy-storage device 108, at least one device 110, and control circuitry 112 may be configured to be disposed in the living subject 103, such as by being sized for being disposed within the living subject 103 or biocompatible with the living subject 103. For example, the optical-electrical converter 104, retroreflector 106, energy-storage device 108, at least one device 110, and control circuitry 112 may be compactly enclosed in a biocompatible protective packaging 115 to package one or more components of the apparatus 102. In an embodiment, the optical-electrical converter 104, retroreflector 106, energy-storage device 108, at least one device 110, and control circuitry 112 may each be individually enclosed in separate biocompatible packaging sections.

The system 100 may further include a selectively positionable external device 116 (e.g., a hand-held device) having an optical power source 118 (e.g., one or more light-emitting diodes, lasers, or other suitable light-emitting devices) configured to output one or more optical signals 120, an optical receiver 122 (e.g., one or more photodiodes) suitable for receiving and converting to electricity location-indicating signals 124 reflected from the retroreflector 106, control circuitry 126 coupled to the optical power source 118 and optical receiver 122, and a user interface 128 coupled to the control circuitry 126. For example, the user interface 128 may be configured as a keypad, touch screen, or other suitable interface that allows the living subject 103 or other user to control the operation of the external device 116. As an example, the external device 116 may be configured as a hand-held device.

Generally, location information about a location of the optical-electrical converter 104 disposed within the living subject 103 may be provided via the one or more reflected location-indicating signals 124. According to an embodiment of an operational method, the one or more optical signals 120 may be transmitted to the living subject 103, responsive to the transmitting, the one or more reflected location-indicating signals 124 may be received, the optical-electrical converter 104 disposed within the living subject 103 may be targeted based at least partially on the received location-indicating signals 124, and one or more optical power signals may be transmitted transdermally into the living subject 103 and to the targeted optical-electrical converter 104.

Still referring to FIG. 1, the operation of the system 100 is described in more detail below. In operation, the optical power source 118 outputs the one or more optical signals 120 as one or more electromagnetic beams at the living subject 103 that are transdermally transmitted through tissue of the living subject 103, through the biocompatible protective packaging 115, and to the retroreflector 106. For example, the one or more optical signals 120 may exhibit at least one infrared or visible peak wavelength that is transdermally transmittable through tissue of the living subject 103. When the one or more optical signals 120 irradiate the retroreflector 106, at least one of the one or more optical signals 120 is reflected from the retroreflector 106 as the one or more location-indicating signals 124, transmitted transdermally out of the living subject 103, and received by the optical receiver 122. The optical receiver 122 converts the one or more received reflected location-indicating signals 124 to one or more electrical signals, and an indication may be provided on the user interface 124 that the one or more optical signals 120 successfully targeted the optical-electrical converter 104. When the one or more optical signals 120 are off target, a weak and diffuse reflected signal may be reflected from tissue of the living subject 103 and received by the optical receiver 122 or no reflected signal may be received indicative of the one or more optical signals 120 not successfully targeting the retroreflector 106. In an embodiment, the external device 116 may be placed in proximity to the retroreflector 106 and abut exterior tissue of the living subject 103. In an embodiment, the power of the one or more optical signals 126 may be sufficient so that the external device 116 may be positioned remote from the living subject 103 and the retroreflector 106 and optical-electrical converter 104 therein.

Responsive to receiving the one or more reflected location-indicating signals 128 and locating the optical-electrical converter 104, the optical power source 118 may be aimed at the located optical-electrical converter 104 to target it and output one or more optical power signals 120' having a significantly higher intensity than that of the one or more optical signals 120 for powering the at least one device 110 of the apparatus 102. The beam size of the one or more optical power signals 120' may be substantially greater than that of the retroreflector 106 so that a relatively large portion of the beam is received by an optical receiving surface of the optical-electrical converter 104, while only a relatively small portion is reflected back toward the external device 116. The one or more optical power signals 120' are transmitted transdermally into the living subject 103 and received by the optical-electrical converter 104. The received one or more optical power signals 120' are converted to electricity that may be stored by the energy-storage device 108, and transmitted to the at least one device 110 as one or more electrical power signals under the control of the control circuitry 112 for powering the at least one device 110. In an embodiment, the optical-electrical converter 104 may be configured to selectively convert specific wavelengths of the one or more optical power signals 120' to electricity.

In the illustrated embodiment, the retroreflector 106 is disposed within the living subject 103 and enclosed in the biocompatible protective packaging 115. However, in one or more embodiments, the retroreflector 106 may be positioned externally, such on the skin of the living subject 103, or on or in clothing worn by the living subject 103.

As previously discussed, the optical-electrical converter 104, retroreflector 106, energy-storage device 108, at least one device 110, and control circuitry 112 may be enclosed in the biocompatible protective packaging 115 that is at least partially transparent to the one or more optical signals 120 and optical power signals 120' output by the external device 116 for locating or powering the at least one device. The biocompatible protective packaging 115 may be formed from a number of different biocompatible polymeric materials, such as at least one of polyxylene, polyethylene, poly(ethylene oxide), polyurethane, or poly(butylene terephthalate). The biocompatible protective packaging 115 may also be formed from a number of different biocompatible ceramics, such as silicate-based ceramics. In an embodiment, the biocompatible protective packaging 115 may be in the form of a biocompatible coating made from at least one of the aforementioned biocompatible polymeric or ceramic materials and formed over a relatively less biocompatible housing that provides structural support for the biocompatible coating or a housing formed from at least one of the aforementioned biocompatible materials.

Figure 2:
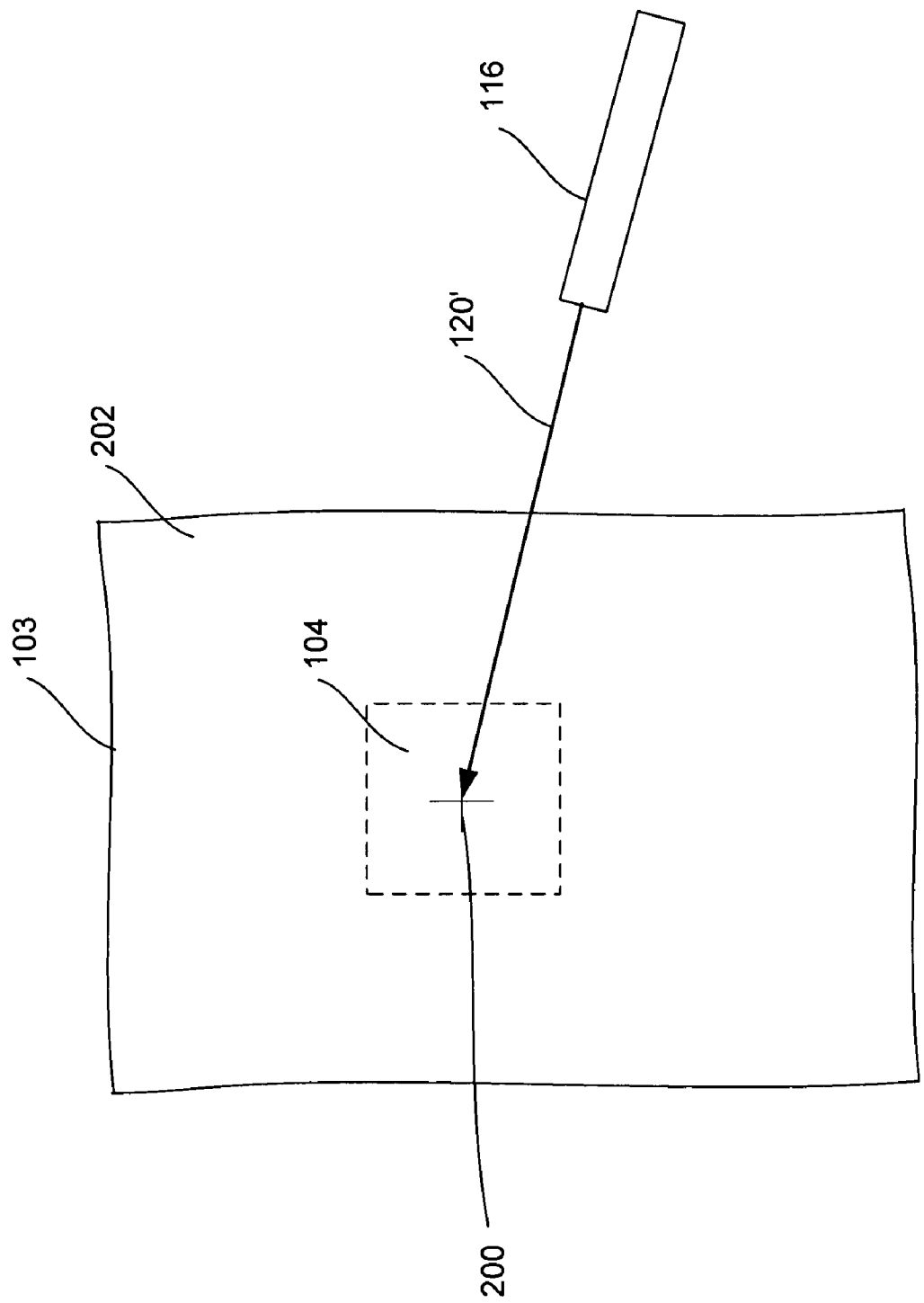
FIG. 2 is an enlarged plan view of an embodiment of a technique for locating an optical-electrical converter disposed within a living subject in which a target is positioned on or below skin of the living subject and in proximity to the optical-electrical converter.

FIG. 2 is an enlarged plan view of an embodiment of a technique for locating the optical-electrical converter 104 disposed within the living subject 103 in which a target 200 is positioned on or below skin 202 of the living subject 103 and in proximity to the optical-electrical converter 104. In the embodiment shown in FIG. 2, the retroreflector 106 shown in FIG. 1 may be omitted. The target 200 may include one or more indicia, such as a tattoo or other suitable marking that is applied to the skin 202 of the living subject and located in proximity to the optical-electrical converter 104 that is disposed below the skin 202. Thus, the target 200 generally marks a location of the optical-electrical converter 104 within the living subject 103.

In practice, the one or more optical power signals 120' output by the external device 116 may be directed generally at the target 200 so that the one or more optical power signals 120' are transmitted transdermally through the skin 202 and other tissue or muscle, and received by the underlying optical-electrical converter 104. As previously described with respect to the embodiment shown in FIG. 1, the received one or more optical power signals 120' may be converted to electricity by the optical-electrical converter 104, stored in the energy-storage device 108 (FIG. 1), and transmitted to the at least one device 110 (FIG. 1) under the control of the control circuitry 112 (FIG. 1).

Although the illustrated embodiment shown in FIG. 2 employs one or more indicia 200 applied to the skin 202 of the living subject 103, other types of indicia may be used. For example, in an embodiment, a marker made from a material (e.g., a polymeric material) that is at least partially transmissive to the one or more optical power signals 120 and visible through the skin 202 may be disposed on the optical-electrical converter 104 and under the skin 202.

Figure 3:
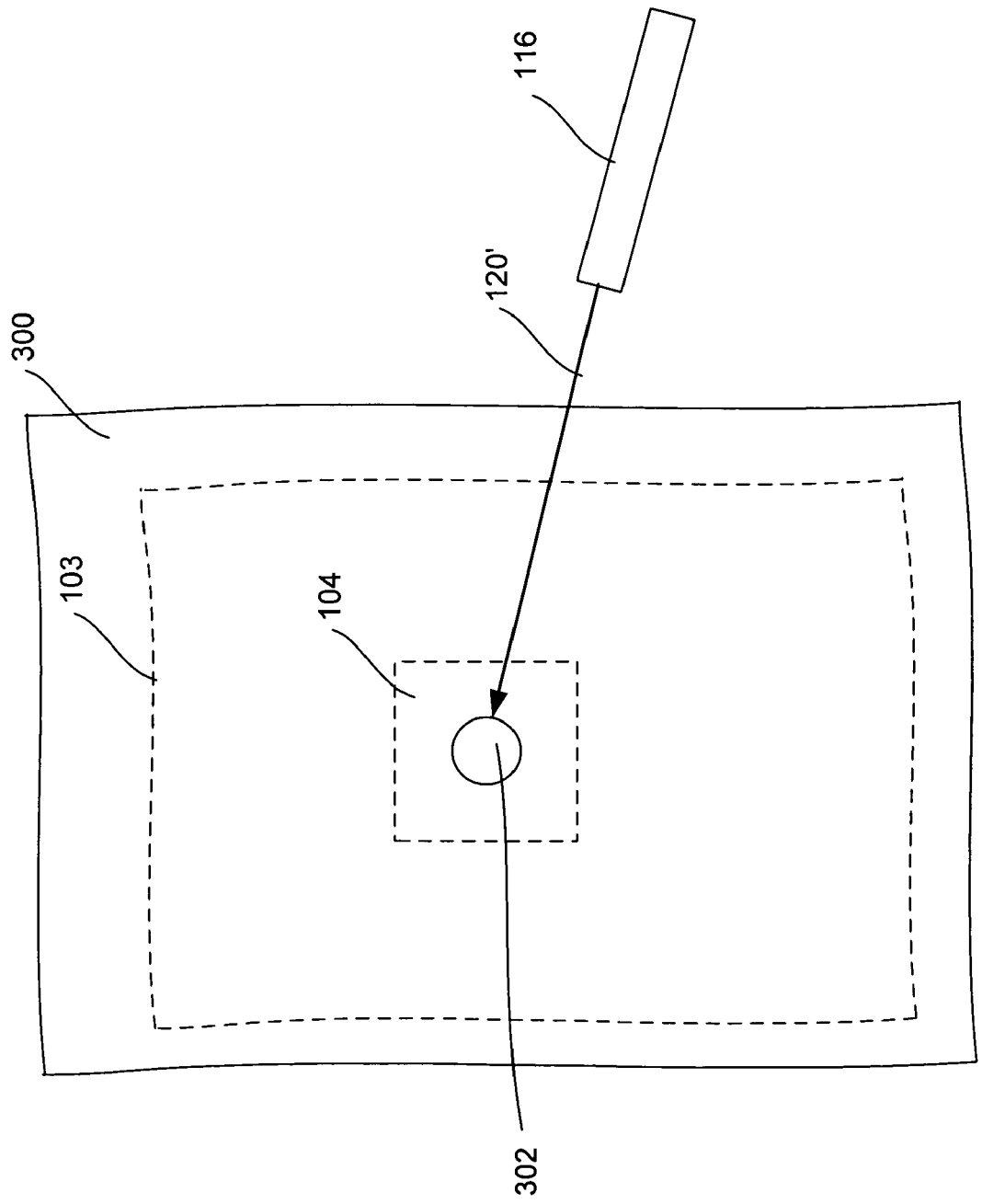
FIG. 3 is an enlarged plan view of an embodiment of clothing to be worn by a living subject that includes one or more indicia located to be in proximity to the optical-electrical converter when worn by the living subject.

FIG. 3 is an enlarged plan view of an embodiment of clothing 300 to be worn by the living subject 103 that includes one or more indicia 302 located to be in proximity to the optical-electrical converter 104 when worn by the living subject 103. In the embodiment shown in FIG. 3, the retroreflector 106 shown in FIG. 1 may be omitted. The one or more indicia 302 may be one or more symbols, such as embroidery, an ink marking, a metal or plastic element, or other suitable identifying feature that forms part of the clothing 300. When the clothing 300 is worn by the living subject 103, the one or more indicia 302 are positioned in proximity to the optical-electrical converter 104 that is disposed within the living subject. Thus, the one or more indicia 302 generally marks a location of the optical-electrical converter 104 within the living subject 103.

In practice, the one or more optical power signals 120' output by the external device 116 may be directed generally at the one or more indicia 302 so that the one or more optical power signals 120' are transmitted transdermally through the clothing 300 and the living subject 103 to be received by the underlying optical-electrical converter 104. The clothing 300 may be made from a material that is substantially transparent to one or more peak wavelengths of the one or more optical power signals 120'. As previously described with respect to the embodiment shown in FIG. 1, the received one or more optical power signals 120' may be converted to electricity by the optical-electrical converter 104, stored in the energy-storage device 108 (FIG. 1), and transmitted to the at least one device 110 (FIG. 1) under the control of the control circuitry 112 (FIG. 1).

Figure 4:
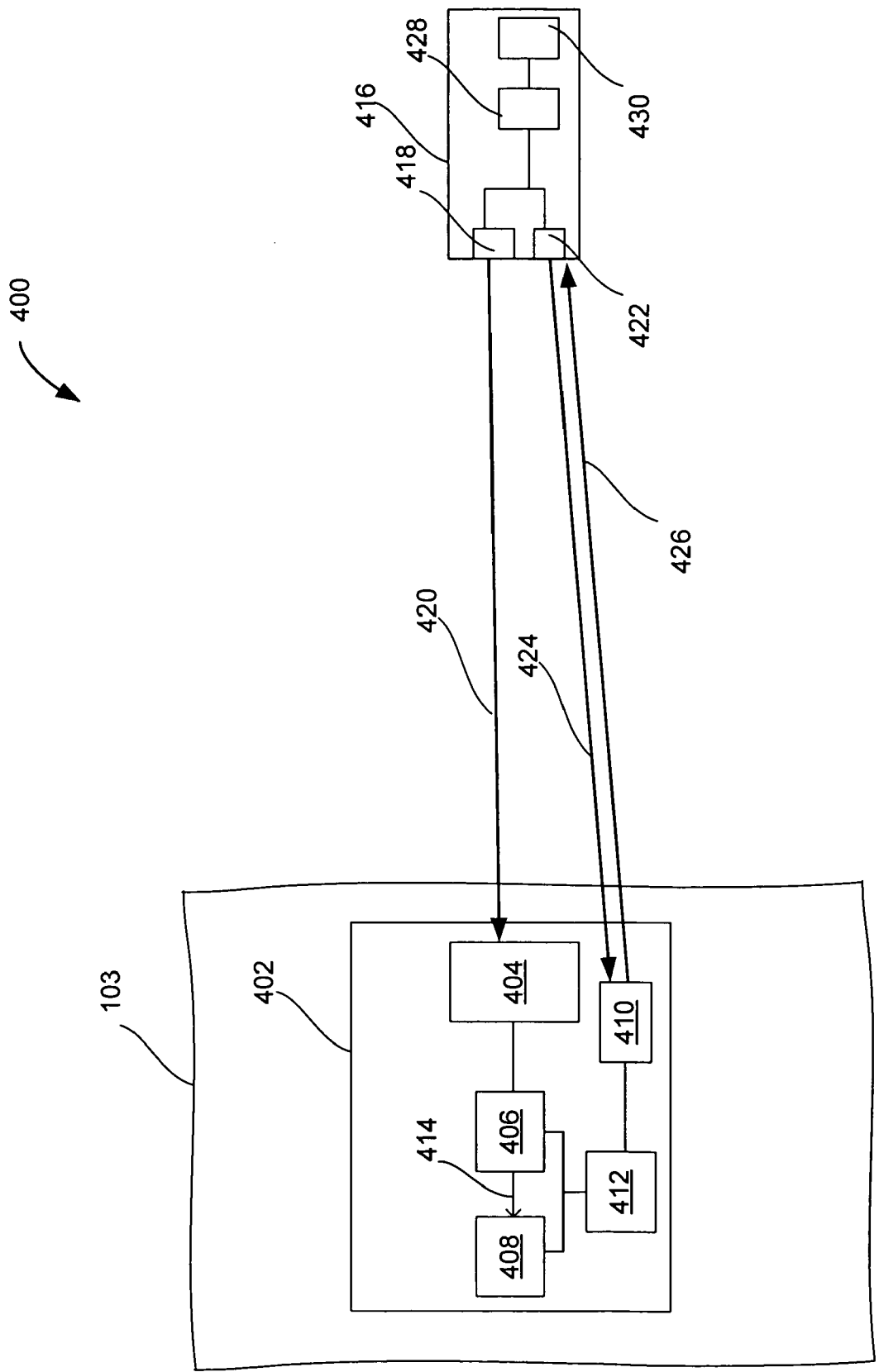
FIG. 4 is a functional block diagram of an embodiment of a system that employs a transceiver disposed within a living subject, which is configured to transdermally transmit one or more location-encoding signals indicative of a location of a optical-electrical converter disposed within the living subject.

FIG. 4 is a functional block diagram of an embodiment of a system 400 that employs a transceiver disposed within a living subject that is configured to transdermally transmit one or more location-encoding signals indicative of a location of an optical-electrical converter disposed within the living subject. The system 400 includes a biocompatible apparatus 402 configured to be disposed within the living subject 103, such as being embedded in tissue, muscle, or bone of a human being. The apparatus 402 includes an optical-electrical converter 404 (e.g., one or more photodiodes), an energy-storage device 406 (e.g., a battery or a capacitive device) coupled to receive and store electricity received from the optical-electrical converter 404, at least one device 408 coupled to the energy-storage device 406, a transceiver 410, and control circuitry 412 coupled to the energy-storage device 406, the at least one device 408, and the transceiver 410. The at least one device 410 may be configured as at least one of a drug delivery device, a micro-electro-mechanical device, a bone extension device, a biosensor, a neurostimulator, or other suitable biomedical device. The control circuitry 412 is configured to control distribution of electricity from the energy-storage device 406 to the at least one device 408 as one or more electrical power signals 414 that power the at least one device 408, and control the operation of the at least one device 408 and the transceiver 410. The various components of the apparatus 402 may be enclosed either collectively or individually in a biocompatible packing similar to or the same as the packaging 115 previously described in the embodiment shown in FIG. 1.

The system 400 may further include a selectively positionable external device 416 having an optical power source 418 (e.g., one or more light-emitting diodes, lasers, or other suitable light-emitting devices) configured to output one or more optical power signals 420, a transceiver 422 configured to output one or more request signals 424 to the transceiver 410 disposed in the living subject 103 and process one or more location-encoding signals 426 output from the transceiver 410 responsive to the request/query 424, control circuitry 428 coupled to the optical power source 418 and transceiver 422, and a user interface 430 coupled to the control circuitry 428. For example, the user interface 428 may be configured as a keypad, touch screen, or other suitable interface that allows the living subject 103 or other user to control the operation of the external device 116.

Generally, location information about a location of the optical-electrical converter 404 disposed within the living subject 103 may be provided via the one or more location-encoding signals 426 output from the transceiver 410 disposed in the living subject 103. According to an embodiment of an operational method, the one or more location-encoding signals 426 that are transmitted from the living subject 103 may be received, the optical-electrical converter 404 may be targeted/located based at least partially on information associated with the one or more received location-encoding signals 426, and one or more optical power signals may be transmitted transdermally into the living subject 103 and to the optical-electrical converter 404 to power the at least one device 408. According to another embodiment of an operational method, the request/query 424 may be transmitted to the living subject 103 and, responsive to the transmitting, the one or more location-encoding signals 426 indicative of the location of the optical-electrical converter 404 may be received. From another perspective and according to another embodiment, the transceiver 422 may receive the request/query 424 and, responsive to the request/query 424, location information about the optical-electrical converter 404 may be transmitted transdermally out of the living subject 103.

Still referring to FIG. 4, the operation of the system 400 is described in more detail below. In operation, the transceiver 422 of the external device 416 may be directed according to input via the user interface 430 to output the one or more request signals 424, which are transmitted transdermally into the living subject 103 and received by the transceiver 410 disposed in the living subject 103. Responsive to the one or more request signals 424, the transceiver 410 outputs the one or more location-encoding signals 426 that have location information of the optical-electrical converter 404 encoded therein to the transceiver 422. The one or more location-encoding signals 426 are transmitted transdermally out of the living subject 103. For example, the one or more request signals 424 or location-encoding signals 426 may be one or more radio-frequency signals or other optical-frequency signals that may exhibit at least one infrared, visible, or non-visible peak wavelength. Further, such one or more request signals 424 or location-encoding signals 426 may be encrypted.

Based at least partially on the received one or more location-encoding signals 426, the control circuitry 428 may compute a beam path and direct the optical power source 418 to output the one or more optical power signals 420 at a location on the living subject 103 so that the optical-electrical converter 404 receives the one or more optical power signals 420 that are transdermally transmitted through the living subject 103. For example, the optical power source 418 may include beam-steering provisions, such as at least one of a diffraction grating, a micro-electro-mechanical scanner, an acoustic-optical device, or an electro-optical device configured to selectively steering the one or more optical power signals 420 based on the computed beam path. The one or more optical power signals 420 are transmitted transdermally through the living subject 103 and received by the optical-electrical converter 404, which converts the one or more optical power signals 420 to electricity that may be stored by the energy-storage device 406. As previously described, the control circuitry 412 may direct the energy-storage device 406 to transmit the one or more electrical power signals 414 to power the at least one device 408.

In an embodiment, the transceiver 410 may be replaced by a transmitter and the transceiver 422 may be replaced by a receiver. The transmitter may be configured to transmit the one or more location-encoding signals 426 periodically or continuously. Such periodically or continuously transmitted one or more location-encoding signals 426 may be received by the receiver of the external device 416 and the control circuitry 428 may compute the target information for the one or more optical power signals 420 based at least partially on the location information encoded in the one or more location-encoding signals 426. In another embodiment, the transceiver 410 may include a radio frequency identification (RFID) tag and the transceiver 422 may be configured to interrogate the RFID tag and receive location information about the optical-electrical converter 404.

Figure 5:
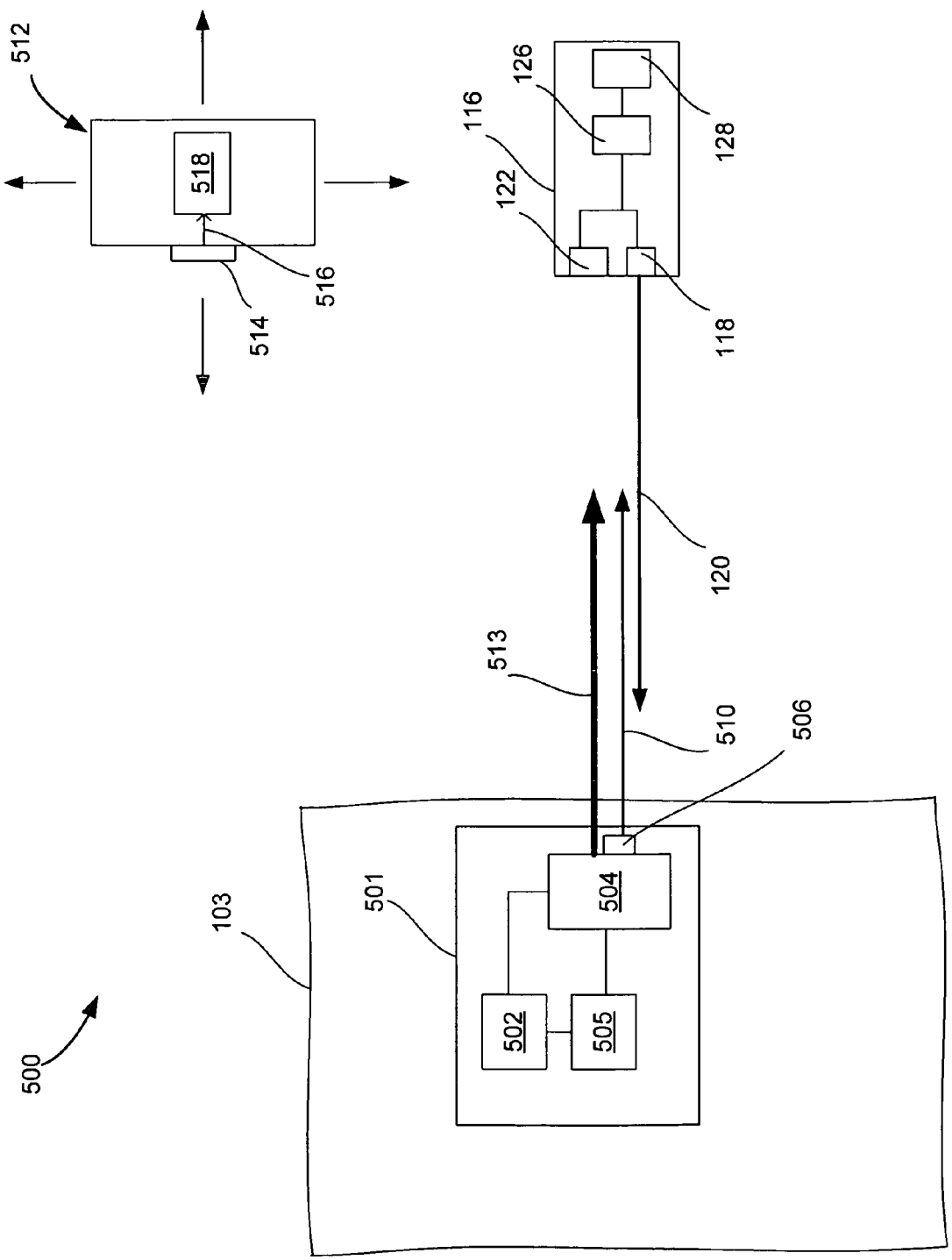
FIG. 5 is a functional block diagram of an embodiment of a system comprising a biocompatible apparatus disposed within a living subject including an electrical-optical converter configured to convert electricity from at least one internal power source to one or more transdermally transmittable optical power signals, and a retroreflector positioned in proximity to the electrical-optical converter to facilitate locating the electrical-optical converter.

FIG. 5 is a functional block diagram of an embodiment of a system 500 configured to transmit one or more optical power signals transdermally out of a living subject to power at least one external device. The system 500 includes an internal optical power transmitter 501 configured to be disposed within a living subject 103, such as being embedded in tissue, muscle, or bone of a human being. The internal optical power transmitter 501 includes a power source 502, an electrical-optical converter 504 operably coupled to the power source 502 to receive electricity (e.g., one or more electrical signals) therefrom, and control circuitry 505 configured to control distribution of electricity from the power source 502 to the electrical-optical converter 504 and the operation of the electrical-optical converter 504. The power source 502, electrical-optical converter 504, and control circuitry 505 may be configured to be disposed in a living subject 103, such as by being sized for being disposed in the living subject 503 or being biocompatible with the living subject 503 and housed individually or collectively in a suitable biocompatible packaging similar to or the same as the biocompatible protective package 115 of FIG. 1. The electrical-optical converter 504 is configured to convert at least a portion of the electricity received from the power source 502 into one or more optical power signals 510 that are transmittable through and out of tissue of the living subject 503 and have a power of at least about 10 μW. In more specific embodiments, the power of the one or more optical power signal 510 output by the electrical-optical converter 504 may range from about 10 μW to about 10 W, about 10 μW to about 1 mW, about 1 mW to about 100 W, and about 100 mW to about 1 W.

According to various embodiments, the power source 502 may include an energy storage device, such as a battery or a capacitive device. In an embodiment, the power source 502 may include an electricity generator configured to convert internal body energy of the living subject 103 to electrical energy. For example, the electricity generator may include at least one of a fluid-flow generator configured to convert internal body fluid motion into electricity, a fluid-pressure generator configured to convert internal fluid pressure into electricity, a muscle-motion generator configured to convert internal muscle motion into electricity, an acceleration-motion generator configured to convert acceleration of the living subject 103 into electricity, or a thermal-electric generator configured to convert internal body heat into electricity.

The system 500 further includes a selectively positionable external device 116 for locating the electrical-optical converter 504 disposed within the living subject 103. Because the structure and functionality of the external device 116 was previously described above, an explanation of the structure and functionality is not repeated in the interest of brevity. In practice, the external device 116 may output one or more optical signals 120 that are reflected from the retroreflector 506 as one or more reflected location-indicating signals 510. As previously described, when the one or more optical signals 120 successfully target the retroreflector 506, the intensity of the one or more reflected location-indicating signals 510 is indicative of the retroreflector 506 being successfully targeted and a location of the electrical-optical converter 504 may be ascertained.

After locating the electrical-optical converter 504, an external device 512 may be positioned to receive one or more optical power signals 513 output by the electrical-optical converter 504. The one or more optical power signals 513 may exhibit at least one infrared, visible, or non-visible peak wavelength. The external device 512 may include a personal electronic device, such as a cell phone, personal data assistant, a video game device, or an electronic medical device. The external device 512 includes an optical-electrical converter 514 (e.g., one or more photodiodes) configured to convert the received one or more optical power signals 513 into one or more electrical power signals 516. For example, the optical-electrical converter 514 may be integrated with or separate from the at least one external device 512. In some embodiments, the optical-electrical converter 514 may be associated with a receiving aperture (e.g., one or more collimation lenses, one or more reflectors, or other focusing optics) that direct the one or more optical power signals 513 to the underlying optical-electrical converter 514 or focus the one or more optical power signals 513 so that substantially all of the optical power is received by the optical-electrical converter 514. The external device 512 further includes control circuitry 518 operably coupled to the optical-electrical converter 514 and configured to control the operation of the at least one external device 512 responsive to receiving the converted one or more electrical power signals 516.

In operation, electrical energy within the living subject 103 is converted into the one or more optical power signals 513, which are transmitted out of the living subject 103 with, for example, a power of at least about 10 μW. More specifically, the electrical-optical converter 504 transmits the one or more optical power signals 513 transdermally through and out of the living subject 103 responsive to instructions from the control circuitry 505, which are received by the optical-electrical converter 514 of the external device 512. For example, the control circuitry 505 may be pre-programmed to direct the electrical-optical converter 504 to output the one or more optical power signals 513 at specific times throughout the day. The one or more optical power signals 513 are received by the optical-electrical converter 514, which converts the one or more optical power signals 513 to one or more electrical power signals 516. The one or more electrical power signals 516 may be used to power the external device 512. For example, the control circuitry 518 receives the one or more electrical power signals 516 and uses the one or more electrical power signals 516 to power and control the operation of the external device 512.

In an embodiment, the external devices 116 and 512 may be integrated into a single device for simplicity. For example, a hand-held electronic device may be integrated with the external device 116 so that the location of the electrical-optical converter 504 can be ascertained to facilitate accurately receiving the one or more optical power signals 513 that can power the hand-held electronic device. It is also contemplated that internal optical power transmitter 501 may include a transceiver and used in conjunction with the external device 416 for locating the electrical-optical converter 504.

Although the illustrated embodiment shown in FIG. 5 employed a retroreflector as a location-indicating aid, in other embodiments, the techniques shown and described with respect to FIG. 4 may be employed. For example, a transceiver may be included in the internal optical power transmitter configured to transmit one or more location-encoding signals responsive to a request/query transmitted transdermally into the living subject from a transceiver incorporated into the external device 116.

Various other embodiments for the internal optical power transmitter 501 are disclosed in U.S. patent application Ser. No. 12/283,911, which was incorporated by reference above.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A method, comprising:
    receiving one or more optical signals reflected from a retroreflector positioned at least proximate to an optical-electrical converter disposed within a living subject and transmitted from the living subject, wherein the one or more optical signals are indicative of a location of the optical-electrical converter;
    targeting the optical-electrical converter disposed within the living subject based at least partially on information associated with the one or more optical signals; and
    transmitting one or more optical power signals transdermally into the living subject and to the targeted optical-electrical converter.

2. The method of claim 1, wherein targeting an optical-electrical converter disposed within the living subject based at least partially on information associated with the one or more optical signals includes aiming an optical power source configured to output the one or more optical power signals at the optical-electrical converter.

3. The method of claim 1, wherein transmitting one or more optical power signals transdermally into the living subject and to the targeted optical-electrical converter includes transmitting the one or more optical power signals at a target positioned at least proximate to the living subject.

4. The method of claim 3, wherein transmitting the one or more optical power signals at a target positioned at least proximate to the living subject includes transmitting the one or more optical power signals at one or more indicia positioned on or below skin of the living subject.

5. The method of claim 3, wherein transmitting the one or more optical power signals at a target positioned at least proximate to the living subject includes transmitting the one or more optical power signals at a target positioned on clothing worn by the living subject.

6. A method, comprising:
- transmitting one or more first signals to a living subject includes transmitting one or more optical signals to the living subject; and
- responsive to the transmitting, receiving one or more second signals transmitted from the living subject indicative of a location of a photonic device disposed within the living subject, the one or more second signals including at least one of the one or more optical signals reflected from a retroreflector positioned at least proximate to the photonic device.

7. The method of claim 6, wherein transmitting one or more first signals to a living subject includes transmitting the one or more first signals transdermally into the living subject.

8. The method of claim 6, wherein receiving one or more second signals transmitted from the living subject indicative of a location of a photonic device disposed within the living subject includes receiving the one or more second signals transmitted transdermally out of the living subject.

9. The method of claim 6, wherein receiving one or more second signals transmitted from the living subject indicative of a location of a photonic device disposed within the living subject includes receiving one or more optical signals transmitted from a transmitter encoding the location of the photonic device.

10. The method of claim 6, wherein transmitting one or more first signals to a living subject includes transmitting the one or more first signals at a target positioned at least proximate to the living subject.

11. The method of claim 10, wherein transmitting the one or more first signals at a target positioned at least proximate to the living subject includes transmitting the one or more first signals at the retroreflector positioned on or below skin of the living subject.

12. The method of claim 10, wherein transmitting the one or more first signals at a target positioned at least proximate to the living subject includes transmitting the one or more first signals at a target positioned on clothing worn by the living subject.

13. The method of claim 6, wherein the photonic device includes an optical-electrical converter.

14. The method of claim 13, further comprising:
- responsive to the receiving the one or more second signals, transmitting one or more optical power signals to the optical-electrical converter.

15. The method of claim 6, wherein the photonic device includes an electrical-optical converter.

16. The method of claim 15, further comprising:
- responsive to the receiving the one or more second signals, receiving one or more optical power signals with the electrical-optical converter.

17. The method of claim 6, wherein the photonic device is biocompatible.

18. A method, comprising:
- receiving one or more first signals transmitted from a living subject, including receiving one or more optical signals reflected from a retroreflector positioned at least proximate to an optical-electrical converter disposed within the living subject and transmitted from the living subject;
- targeting the optical-electrical converter disposed within the living subject based at least partially on information associated with the one or more first signals; and
- transmitting one or more optical power signals transdermally into the living subject and to the targeted optical-electrical converter.

19. The method of claim 18, wherein receiving one or more first signals transmitted from a living subject includes receiving one or more first optical signals encoding a location of the optical-electrical converter.

20. The method of claim 18, wherein receiving one or more first signals from a living subject includes receiving one or more first radio-frequency signals encoding a location of the optical-electrical converter.

21. The method of claim 18, wherein targeting the optical-electrical converter disposed within the living subject based at least partially on information associated with the one or more first signals includes aiming an optical power source configured to output the one or more optical power signals at the optical-electrical converter.

22. The method of claim 18, wherein transmitting one or more optical power signals transdermally into the living subject and to the targeted photonic device includes transmitting the one or more optical power signals at a target positioned at least proximate to the living subject.

23. The method of claim 22, wherein transmitting the one or more optical power signals at a target positioned at least proximate to the living subject includes transmitting the one or more optical power signals at one or more indicia positioned on or below skin of the living subject.

24. The method of claim 22, wherein transmitting the one or more optical power signals at a target positioned at least proximate to the living subject includes transmitting the one or more optical power signals at a target positioned on clothing worn by the living subject.

* * * * *